US012586669B2

(12) United States Patent
Xie et al.

(10) Patent No.: US 12,586,669 B2
(45) Date of Patent: Mar. 24, 2026

(54) ELECTRONIC BINDER SYSTEM (EBINDER) FOR PROCESSING SOURCE DATA TO EDC SYSTEMS

(71) Applicants: Tai Xie, Boynton Beach, FL (US); Richard Xue, Plainsboro, NJ (US)

(72) Inventors: Tai Xie, Boynton Beach, FL (US); Richard Xue, Plainsboro, NJ (US)

( * ) Notice: Subject to any disclaimer, the term of this patent is extended or adjusted under 35 U.S.C. 154(b) by 0 days.

(21) Appl. No.: 19/105,682

(22) PCT Filed: Aug. 23, 2023

(86) PCT No.: PCT/US2023/030961
§ 371 (c)(1),
(2) Date: Feb. 21, 2025

(87) PCT Pub. No.: WO2024/044273
PCT Pub. Date: Feb. 29, 2024

(65) Prior Publication Data
US 2026/0011421 A1    Jan. 8, 2026

Related U.S. Application Data

(60) Provisional application No. 63/400,158, filed on Aug. 23, 2022.

(51) Int. Cl.
*G16H 15/00*     (2018.01)
*G06F 21/60*     (2013.01)
(Continued)

(52) U.S. Cl.
CPC ........... *G16H 15/00* (2018.01); *G06F 21/602* (2013.01); *G06F 21/6245* (2013.01);
(Continued)

(58) Field of Classification Search
CPC ........ G16H 15/00; G16H 10/20; G16H 70/20; G06F 21/602; G06F 21/6245;
(Continued)

(56) References Cited

U.S. PATENT DOCUMENTS

2016/0210427 A1     7/2016   Mynhier et al.
2017/0147792 A1*    5/2017   Ikeguchi ................ G16H 10/20
(Continued)

OTHER PUBLICATIONS

Vcelak, Elsevier, 2019, pp. 128-137.*
(Continued)

*Primary Examiner* — Michael I Ezewoko
(74) *Attorney, Agent, or Firm* — LAW OFFICES OF ALBERT WAI-KIT CHAN, PLLC

(57) ABSTRACT

The present invention provides a method and system for automatically and seamlessly processing clinical trial source data into electronic data capture (EDC) systems. In one embodiment, a file structure is defined for an electronic binder system (eBinder); source data is uploaded to the eBinder; the source data is encrypted, Patient Identifiable Information in the source data is masked; the source data is converted into machine readable plain text in the JavaScript Object Notation (JSON) format using Natural Language Processing (NPL) technologies; the JSON data is converted into tabulated machine readable data in the HyperText Markup Language (HTML) format using NPL technologies; the HTML data is converted into machine understandable data using NPL technologies; the machine understandable data is populated into EDC datasets using NPL technologies; the source data and converted data are displayed side-by-side for source data verification; and a platform is provided for regulatory data verification or auditing.

14 Claims, 14 Drawing Sheets

(51) Int. Cl.

| | |
|---|---|
| *G06F 21/62* | (2013.01) |
| *G16H 10/20* | (2018.01) |
| *G16H 70/20* | (2018.01) |
| *G06F 40/151* | (2020.01) |
| *G06F 40/174* | (2020.01) |
| *G06F 40/177* | (2020.01) |
| *G06F 40/232* | (2020.01) |
| *G06V 30/19* | (2022.01) |

(52) U.S. Cl.
CPC ............. *G16H 10/20* (2018.01); *G16H 70/20* (2018.01); *G06F 40/151* (2020.01); *G06F 40/174* (2020.01); *G06F 40/177* (2020.01); *G06F 40/232* (2020.01); *G06V 30/19* (2022.01)

(58) Field of Classification Search
CPC .... G06F 40/232; G06F 40/151; G06F 40/177; G06F 40/174; G06V 30/19
See application file for complete search history.

(56) References Cited

U.S. PATENT DOCUMENTS

| | | | |
|---|---|---|---|
| 2020/0402625 A1 | 12/2020 | Aravamudan et al. | |
| 2021/0210175 A1* | 7/2021 | Sethre | G16H 15/00 |
| 2021/0210184 A1 | 7/2021 | Lucas et al. | |

OTHER PUBLICATIONS

Newhauser, Elsevier, 2014, pp. 134-140.*
International Search Report dated Nov. 30, 2023, Tai Xie et al., for "An Electronic Binder System (Ebinder) for Processing Source Data to EDC Systems", International Application No. PCT/US23/30961, filed Aug. 23, 2023.
Written Opinion of the International Searching Authority dated Nov. 30, 2023, Tai Xie et al., for "An Electronic Binder System (Ebinder) for Processing Source Data to EDC Systems", International Application No. PCT/US23/30961, filed Aug. 23, 2023.

* cited by examiner

Figure 2

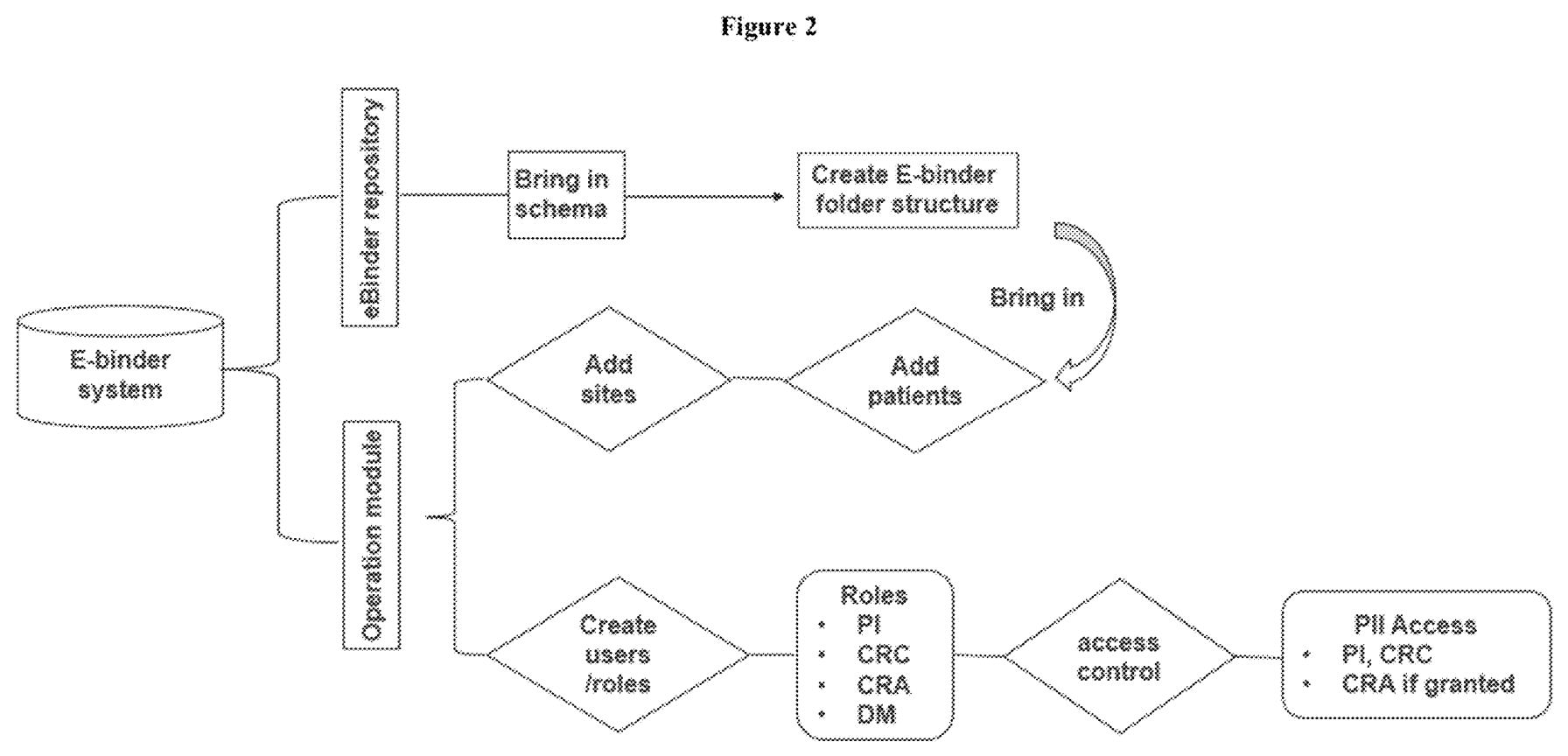

Create E-binder folder structure

Bring in

Add patients

Bring in schema

Add sites eBinder repository

Operation module

E-binder system

Roles
PI
CRC
CRA
DM

PII Access
PI, CRC
CRA if granted access control

Create users /roles

Figure 3

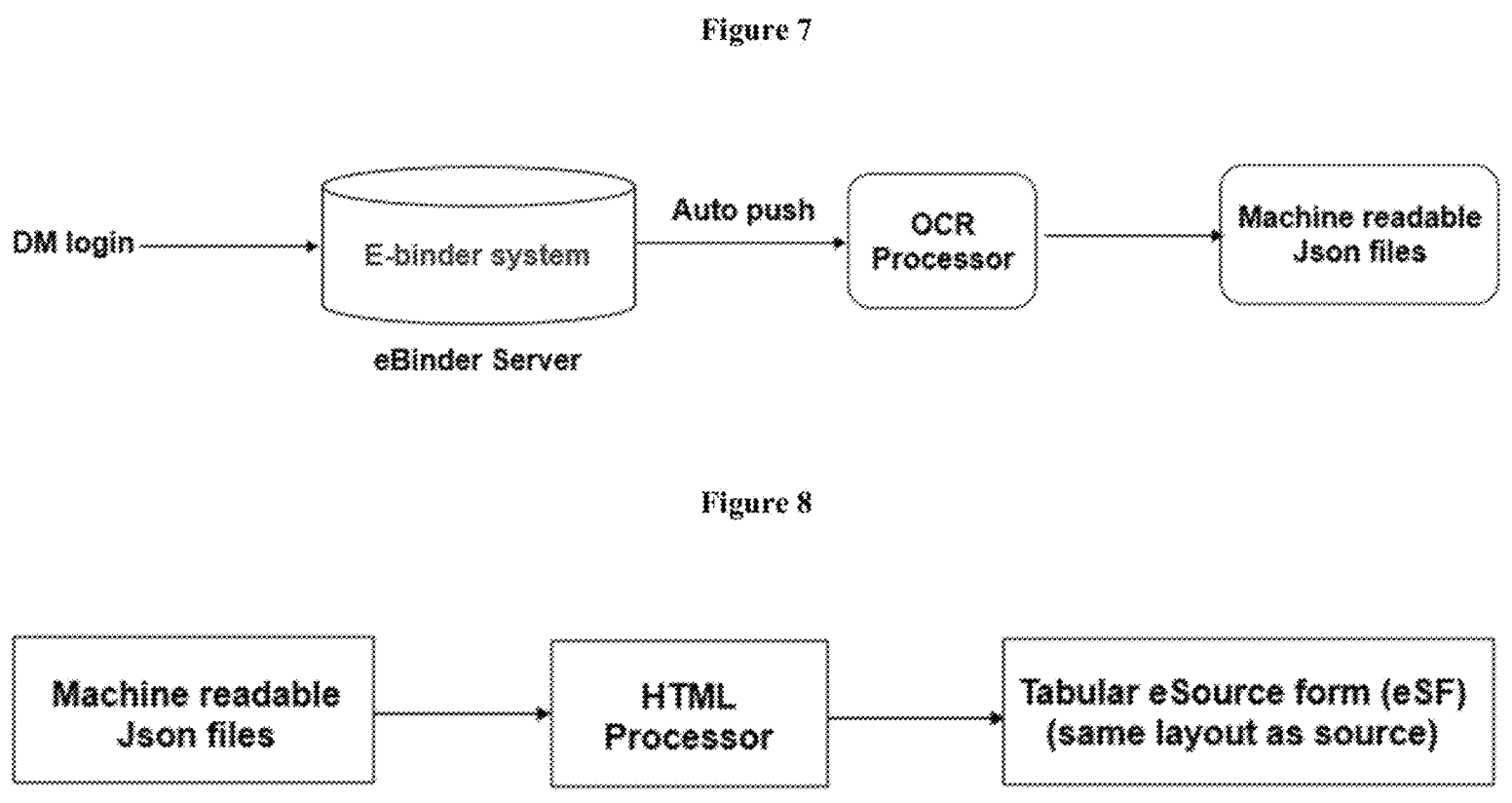

DM login → E-binder system / eBinder Server → Auto push → OCR Processor → Machine readable Json files

Figure 7

Machine readable Json files → HTML Processor → Tabular eSource form (eSF) (same layout as source)

Figure 11:
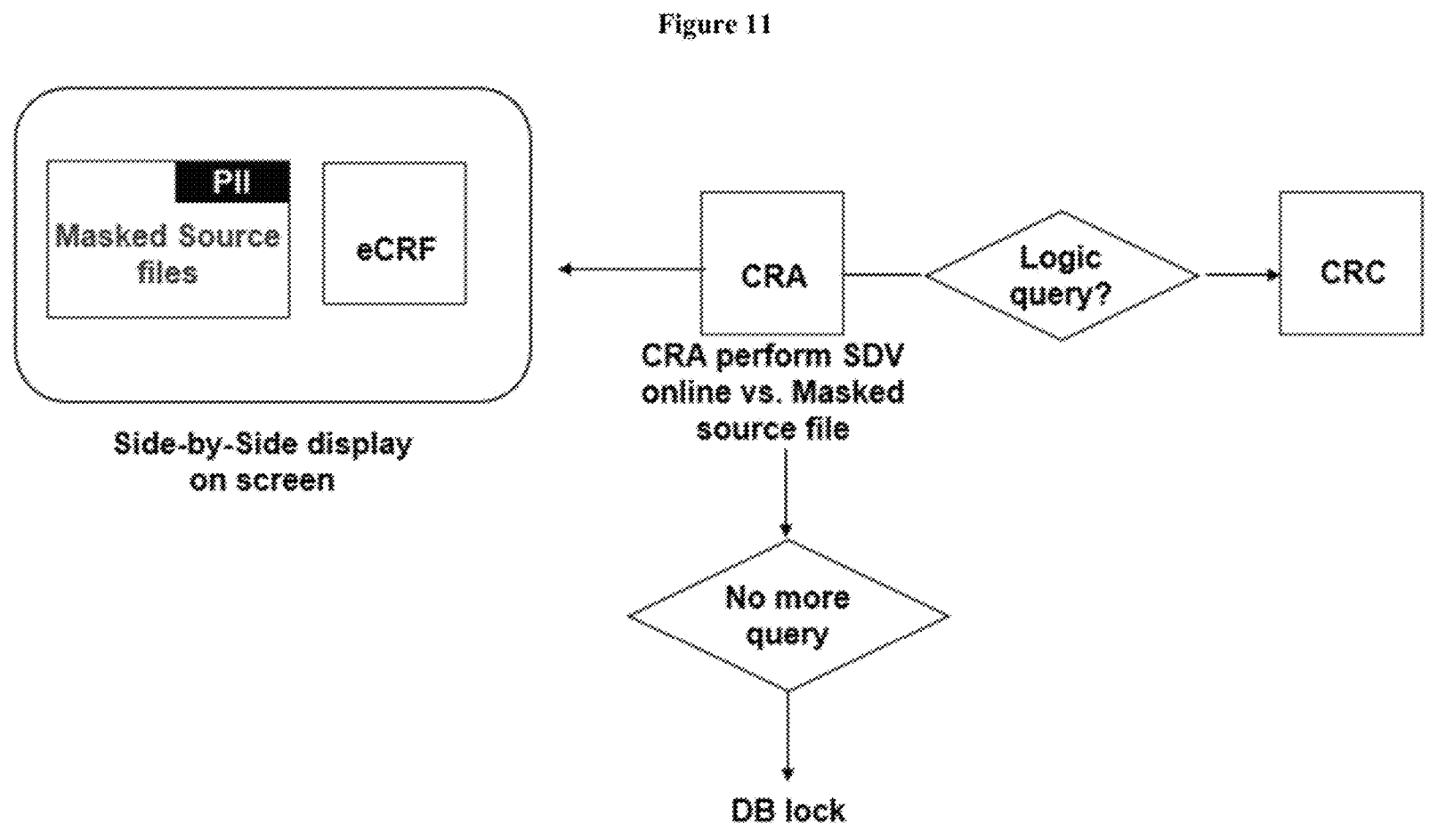

CRC

Logic query?

CRA

CRA perform SDV online vs. Masked source file

No more query

DB lock eCRF

PII

Masked Source files

Side-by-Side display on screen

Figure 13

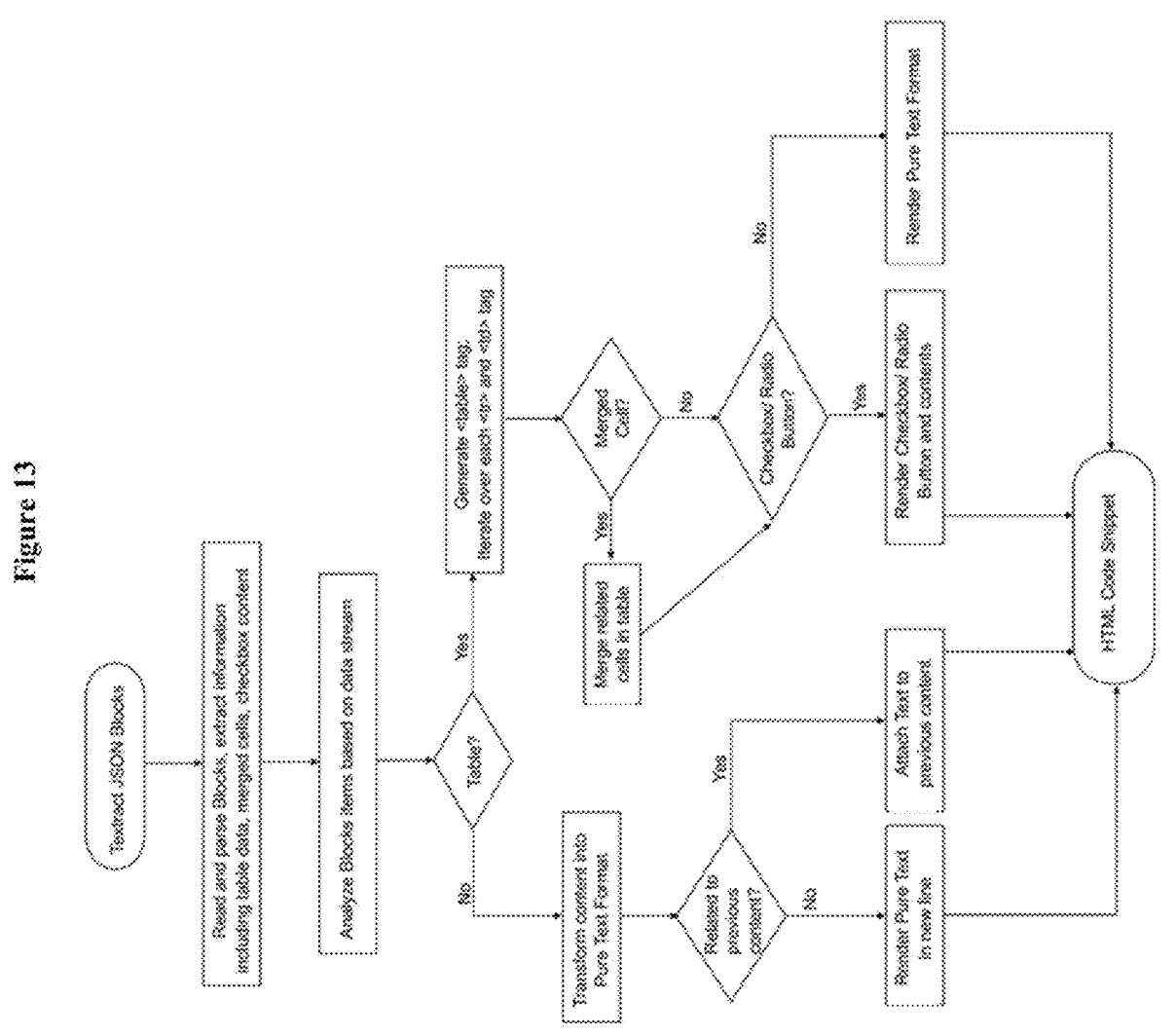

Extract JSON Blocks

Read and parse Blocks, extract information including table data, merged cells, checkbox content Analyze Blocks items based on data stream Table?

Generate <table> tag, iterate over each <tr> and <td> tag

Merged Cell?

Merge relative cells in table

Checkbox/ Radio Button?

Render Checkbox/ Radio Button and contents

Render Pure Text Format

Transform content into Pure Text Format

Related to previous content?

Attach Text to previous content

Render Pure Text in new line

HTML Codes Snippet

Figure 14

Subject Visit

| Visit/Period/Day | Date of Visit (dd/mmm/yyyy) | Time of Visit* (HH:MM) | Done by Initial | Verified by Initial & Date (dd/mmm/yyyy) |
|---|---|---|---|---|
| Screening | 27/JAN/2021 | 07:58 | | 07Feb2021 |
| Visit 1 Day 1 | 01/FEB/2021 | 07:56 | | 07Feb2021 |
| Visit 2 Day 8 | 08/Feb/2021 | 07:57 | | 09Feb2021 |
| Visit 3 Day 15 | 15/Feb/2021 | 07:56 | | 16Feb2021 |
| Visit 4 Day 22 | 22/Feb/2021 | 08:05 | | 22Feb2021 |
| Visit 5 Day 29 | 01/MAR/2021 | 08:16 | | 07Mar2021 |
| Visit 6 Day 36 | 08/MAR/2021 | 08:04 | | 08Mar2021 |

Figure 15

| Visit/Period/ Protocol Time | Actual Date (dd/mmm/yyyy) Actual Time HH:MM | Position | Arm Used | Blood Pressure (mm Hg) e.g. 120/60 | Pulse Rate (bpm) e.g. 70 | Oxygen Saturation SPO2 (%) e.g. 99 | Temperature (°C) e.g. 36.9 | Done by Initial | Verified by Initial & Date (dd/mmm/yyyy) |
|---|---|---|---|---|---|---|---|---|---|
| Pre dose | 01/Feb/2021 08:58 | ☐ Supine ☒ Sitting ☐ Standing | ☐ R ☒ L | 98/56 | 71 | | ☐ Temporal artery ☐ Others#: | | 02Feb2021 |
| | | | Cuff Size ☐ S ☒ M ☐ L | Equipment Lilly Tag e.g., 005F | CBP012 | | Thermometer Lilly Tag # e.g. 005F | | |

| Visit/Period/ Protocol Time | Actual Date (dd/mmm/yyyy) Actual Time HH:MM | Position | Arm Used | Blood Pressure (mm Hg) e.g. 120/60 | Pulse Rate (bpm) e.g. 70 | Oxygen Saturation SPO2 (%) e.g. 99 | Temperature (°C) e.g. 36.9 | Done by Initial | Verified by Initial & Date (dd/mmm/yyyy) |
|---|---|---|---|---|---|---|---|---|---|
| Pre dose | 01/Feb/2021 08:58 | ☐ Supine ☒ Sitting ☐ Standing | ☐ R ☒ L | 98/56 | 71 | | ☐ Temporal artery ☐ Others#: | | 02Feb2021 |
| | | | Cuff Size ☐ S ☒ M ☐ L | Equipment Lilly Tag e.g., 005F | CBP012 | | Thermometer Lilly Tag # e.g. 005F | | |

Figure 16

Subject ID 002-001

| | Visit 1 |
| --- | --- |

Vital Sign

| Planned Time Point | Date Time | Position | Systolic Blood Pressure | Diastolic Blood Pressure | Manual Hear Rate |
| --- | --- | --- | --- | --- | --- |
| Predose | 01/Feb/2021 ○ 8:58 | Sitting | 98 ○ mmHg | 56 ○ mmHG | 71 bpm |

ELECTRONIC BINDER SYSTEM (EBINDER) FOR PROCESSING SOURCE DATA TO EDC SYSTEMS

CROSS-REFERENCE TO RELATED APPLICATIONS

This application 18 the National Stage of International Application No. PCT/U823/30961, filed Aug. 23, 2023, which claims benefit of U.S. Provisional Application No. 63/400,158, filed Aug. 23, 2022. The entire contents and disclosures of the preceding applications are incorporated by reference into this application. Throughout this application, various publications are cited. The disclosures of these publications in their entireties are hereby incorporated by reference into this application to more fully describe the state of the art to which this invention pertains.

FIELD OF THE INVENTION

The present invention relates to methods and systems for automatically and seamlessly processing source data in clinical trials into clinical trial electronic data capture (EDC) systems.

BACKGROUND OF THE INVENTION

Electronic Data Capture (EDC) systems are commonly used in clinical trials to collect, manage and store clinical trial data. Traditionally, study sites collect patient data, according to study protocol, on site specific source data collection forms (SDCFs) and keep them in a physical patient binder. A Clinical Research Coordinator (CRC) then manually enters data from SDCFs into corresponding case report forms (CRFs) in a clinical trial data management system typically called Electronic Data Capture. This manual data entry process at the site level can lead to transcription errors and is extremely inefficient. As an important quality control process in clinical trials, the Clinical Research Organization (CRO) sends clinical trial monitors, also known as clinical research associates (CRAs), to study sites to perform manual source data verification (SDV). SDV is a tedious, time-consuming, and costly process.

In 2013, the United States Food and Drug Administration (FDA) issued a guidance document to the industry [1] on Electronic Source Data in Clinical Trials, wherein the agency listed requirements for capturing source data electronically and transmitting it to the electronic CRF (eCRF). Those requirements included:

Eliminating unnecessary duplication of data;
Reducing the possibility for transcription errors;
Encouraging entering source data during a subject's visit, where appropriate;
Eliminating transcription of source data prior to entry into an eCRF;
Facilitating remote monitoring of data;
Promoting real-time access for data review; and
Facilitating the collection of accurate and complete data.

There is no comprehensive method or system capable of meeting the FDA's requirements. TransCelerate BioPharma Inc., a non-profit organization for leading biopharma companies, published two papers [2, 3] to encourage member companies to initiate the development of methods for optimizing the use of electronic source data in clinical trials. The papers acknowledged that "data collection methods and technology have not been utilized to their fullest capability, and transcription between electronic systems continues to be the norm".

Developing a system for automatically processing the source data into remotely accessible EDC, thereby eliminating transcription errors and in-person SDV, would address needs that are currently unmet in the field. Namely, addressing such needs could greatly improve data quality and clinical trial efficiency, resulting in better clinical trials and enormous cost saving.

The source data at study site level may contain personal identifiable information (PII) or private health information, both of which need to be protected in accordance with HIPAA, GDPR, and other regulations. Accordingly, care must be taken when transmitting, processing, and storing such data.

Prior to processing the source data, any PII contained in the source must be de-identified or de-sensitized. This step is called "masking" and can be done manually by site personnel such as the CRC or Study Coordinator (SC). Masking frequently involves redacting the sensitive data. However, manually masking source data typically requires an incredible amount of work. Therefore, a means to automatically mask PII would benefit the field tremendously. While such masking must protect PII from unauthorized access, it must still allow the SC and CRA to view the unmasked source data for verification purposes. Confidential data can be transmitted or retrieved via a secure process such as HTTPS (secure communication HTTP protocol for the internet) or SFTP (the secure FTP server process). However, protecting confidential data in transit alone is insufficient. Confidential data must also be protected at rest on a server or wherever else it may be stored. HTTPS or SFTP alone would not solve this security issue. Therefore, additional security measures are needed.

The transmitted source files are often in image format and may contain more information than what is required by CRFs. In order to automatically process the source data into EDC, the challenges remain of how to convert the images into machine-readable data, how to make the machine-readable data machine understandable, and how to accurately enter them into EDC.

Source data and source files are exchangeable in this application.

SUMMARY OF THE INVENTION

The present invention provides for a method and a system for transferring and directly processing clinical trial source data into clinical trial database (EDC) including an eBinder system in electronic communication with a web application for receiving source data from study sites, an encryption module for encrypting uploaded source data, a PII masking module for auto-masking Patient Identifiable Information (PII), an eBinder database for storing data, an Optical Character Recognition (OCR) module for converting images (the Source File) into machine readable plain text, a Prompt Engineering (PE, a.k.a in-context learning) module for Generative Pre-Trained Transformer (GPT) to transfer plain text into machine understandable data, and populate SD into the corresponding data field in case report forms (CRFs).

BRIEF DESCRIPTION OF THE DRAWINGS

FIG. 2 illustrates eBinder system.
FIG. 3 illustrates the eBinder system's structure.

FIG. 7 illustrates processing images into machine readable plain text files.

FIG. 8 illustrates formatting machine readable JSON to tabular e-Source Form (eSF).

FIG. 11 illustrates CRA performing remote Source Data Verification (SDV).

FIG. 13 illustrates the processing of JSON files to HTML.

FIG. 14 shows a sample of masked source file.

FIG. 15 illustrates transcription from source file to HTML tabulated e-Source Form.

FIG. 16 illustrates transcription from HTML tabulated e-Source Form to EDC.

DETAILED DESCRIPTION OF THE INVENTION

Figure 1:
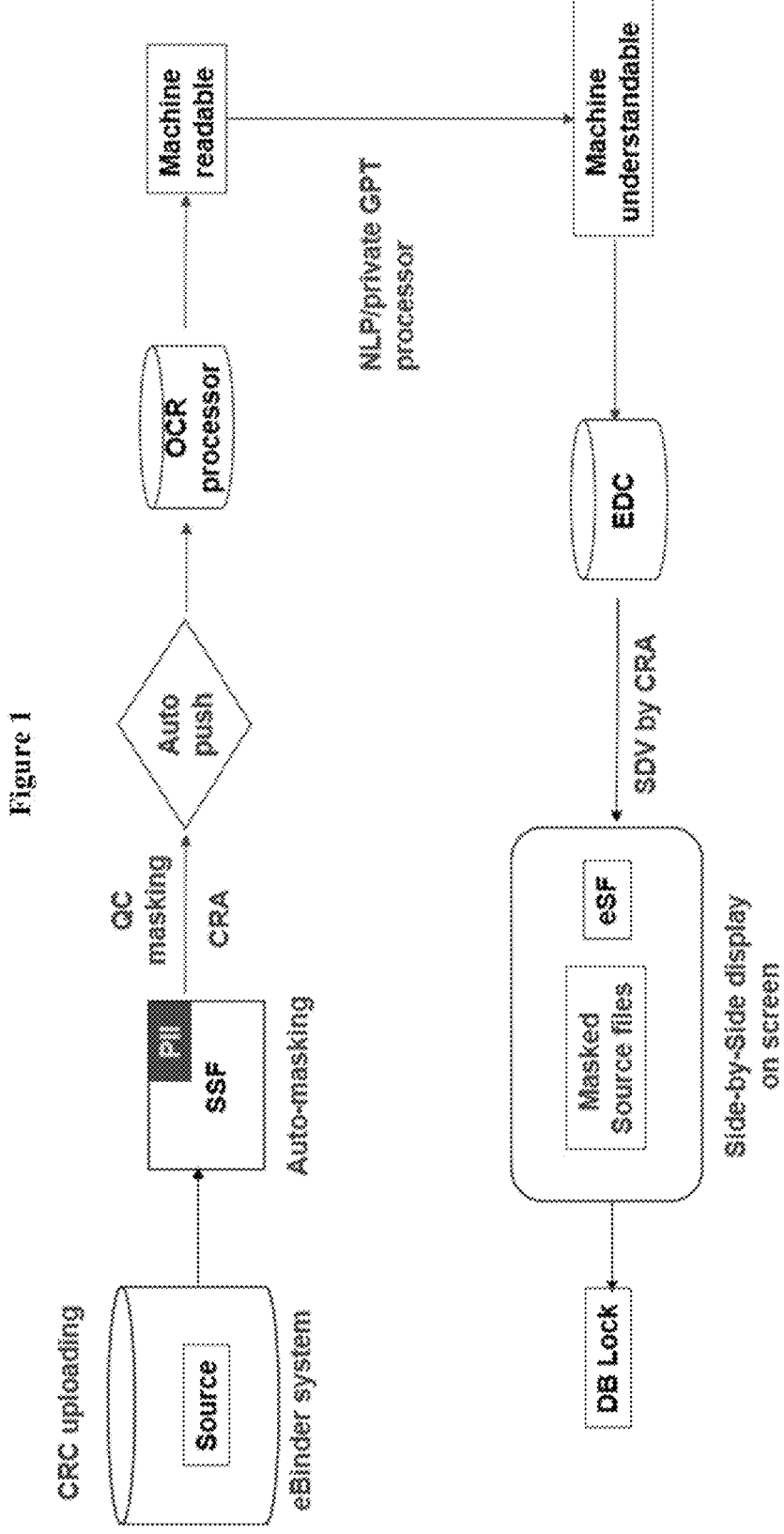
FIG. 1 shows an overview of eBinder Processing.
Figure 4:
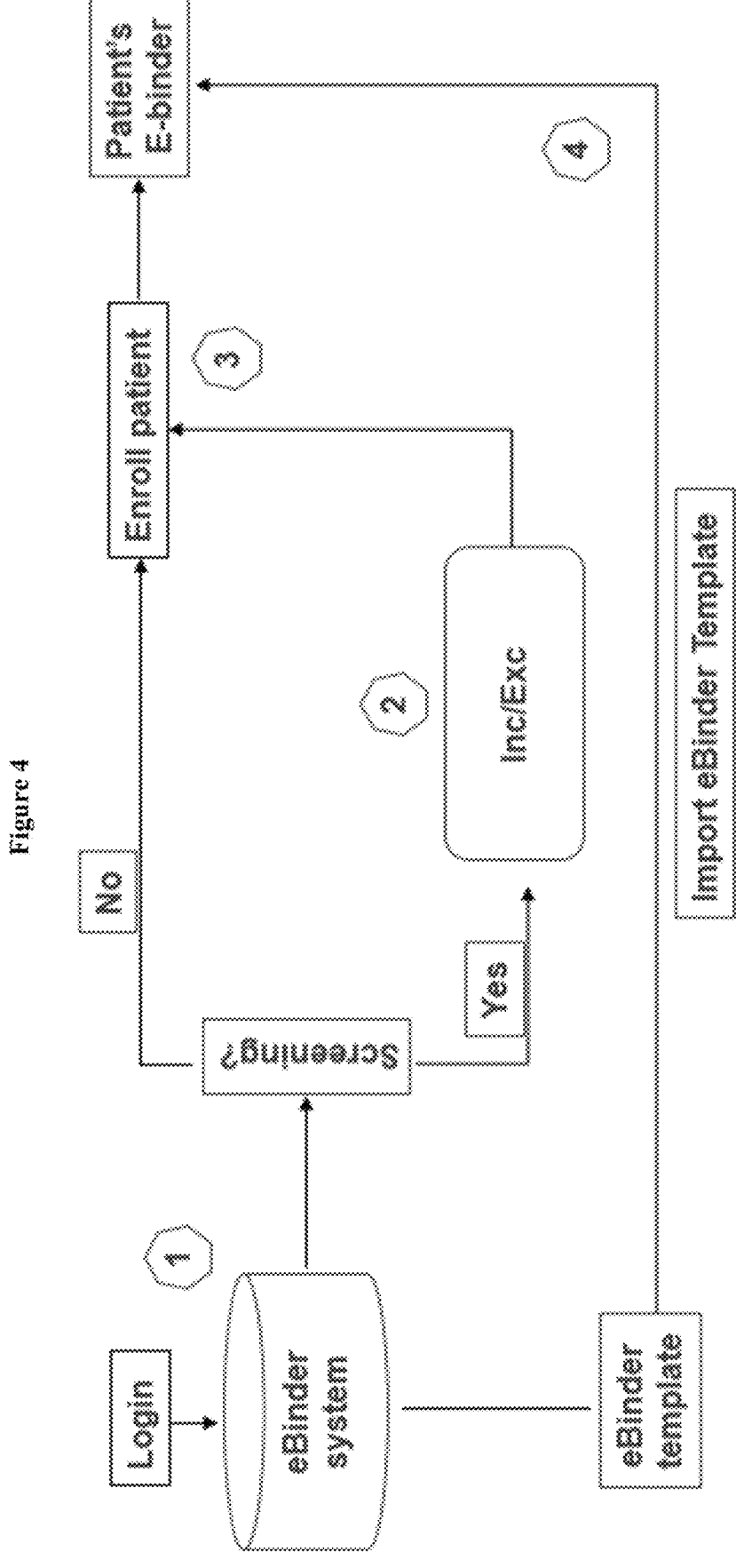
FIG. 4 illustrates Patient Enrollment Process at Site Level.

The present invention provides methods and systems for securely transferring clinical trial source data to Electronic Data Capture (EDC) clinical trials systems. Essentially, the present invention protects private data such as Personal Identifiable Information (PII) and other sensitive information which needs to be protected when it is accessed from various devices and transferred between systems. The present invention allows various types of clinical trial EDC systems to use an "eBinder" system to upload clinical trials source data without compromising the security of PII and other private information contained therein.

The present invention provides multiple processes further described below, including, but not limited to, creating an electronic source data management platform called an "eBinder" into which study sites may upload source data, automatically masking PII upon upload, encrypting the entirety of the original source data stored in eBinder viewable only by CRC and/or CRA, converting images of source data into machine-readable data, converting the machine-readable data into machine-understandable data, storing the converted data in a secured database, mapping the converted data to a corresponding clinical database, validating the automatically fed data against the original source data, and creating access for regulatory inspection or third-party auditing.

In one embodiment, this invention provides a method for automatically and seamlessly converting clinical trial source data into a key-value structured datasets and processing it into EDC datasets. The method comprises defining a file structure for storing source data in an eBinder system, extracting source data from a plurality of sources, encrypting data using a dual-key encryption algorithm in which a private key held by data owner for PII and shared-key for non-PII, masking of PII by a CRC and performing quality control of said masking by a CRA, converting masked source file images into machine readable plain text in the JavaScript Object Notation (JSON) format using OCR technology, transforming said JSON format data into tabulated machine readable data in the HyperText Markup Language (HTML) format, using NLP technologies to correct format or spelling errors for transforming the machine-readable HTML data into machine understandable data, populating selected source data into correct data filed in CRFs of EDC using AI technology, displaying source files and converted data side-by-side for being able to conduct remote SDV, and providing a platform for verifying submission data against source files for regulatory review or auditing purposes.

In one embodiment, this invention provides a method for automatically and seamlessly converting clinical trial source data into a key-value structured datasets and processing it into EDC datasets. The method comprises defining a file structure for storing source data in an eBinder system, extracting source data from a plurality of sources, encrypting said source data using an encryption algorithm, masking PII, verifying the masking of said PII, converting said source file images into machine readable plain text using OCR technology, correcting any formatting or spelling errors in said machine readable plain text using NPL, transforming said machine readable plain text into tabulated machine readable text using NPL, converting said tabulated machine readable plain text into machine understandable plain text using NPL, populating eCRFs using said machine understandable plain text, displaying said populated eCRFs and associated source data side-by-side, and verifying said eCRFs against said associated source data.

In one embodiment, source data are encrypted using a dual-key encryption algorithm.

In one embodiment where source data are encrypted using a dual-key encryption algorithm, one encryption key permits access to unmasked data and the second encryption key permits access to masked data.

In one embodiment, the machine readable plain text is in the JSON format.

In one embodiment, the tabulated machine readable plain text is in the HTML format.

In one embodiment, the NPL processing is conducted using a GPT process.

In one embodiment, eCRFs and associated source data are verified using a web-based platform.

In one embodiment, FIG. 1 illustrates an overview of the entire Direct Source Data to EDC (DSDE) process for clinical trials.

When clinical trial documents are uploaded to the eBinder system, the original documents are encrypted with an advanced encryption algorithm and stored on a Virtual Private Cloud (VPC) server. The encryption key is only available to the study administrators. While uploading the original clinical trial documents, the eBinder system also automatically masks all PII data and stores the masked documents on the VPC server. The masked documents are then transmitted to Amazon Web Service (AWS) S3 buckets for an Optical Character Recognition (OCR) process. The OCR process extracts plain text data from the masked documents in the S3 buckets and stores them in the Cloud Database from which they can be retrieved for clinical trial researchers to view via an eBinder UI Portal.

In the present invention, the system includes an eBinder system (FIG. 2) in electronic communication with a web application for receiving data from clinical trials studies, an encryption module (FIG. 5) for encrypting documents, a PII masking module (FIG. 6) for masking data, an eBinder database which can be hosted as Cloud Database for storing data, an OCR module (FIG. 7) for converting source file images into machine readable plain text in JSON format, an HTML module (FIG. 8) for formatting machine readable JSON files into tabulated e-Source Forms (eSFs) with the same layout as the original source files, a Natural Language Processing (NLP)/Generative Pre-Trained Transformer (GPT) module (FIG. 9) for converting eSFs into machine understandable data and populating selected source data into corresponding data fields in eCRFs and EDC datasets.

Figure 3:
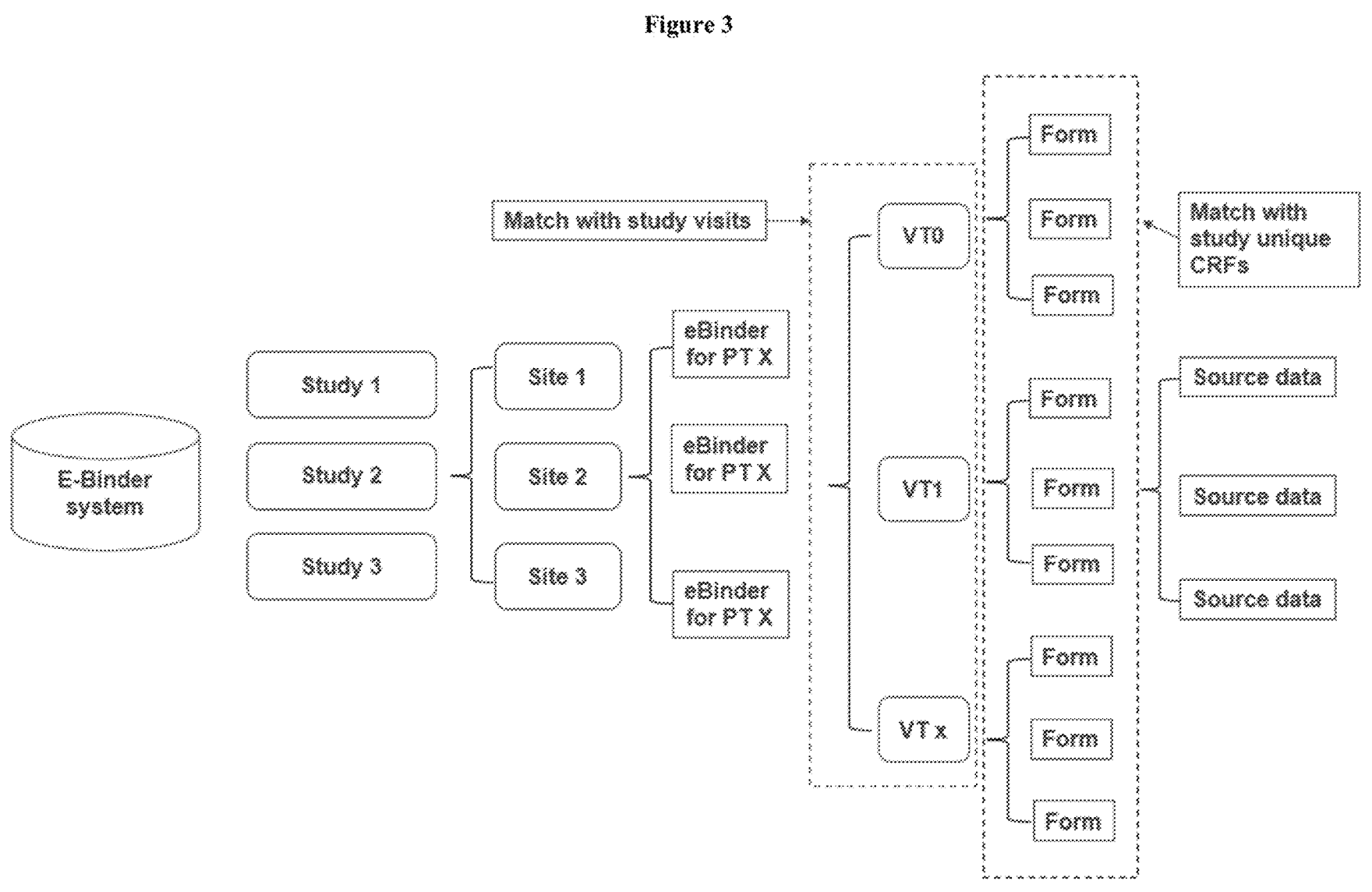

Once the study protocol is finalized, an eBinder system can be built according to the study schema defined in the protocol. The study schema consists of Case Report Forms (CRF) and timepoints (Visits) where the CRFs will be collected. In one embodiment, the eBinder system comprises an eBinder database and an operation module (FIG. 1). The eBinder database is for storing source files and data that contains eBinder folder structure according to study schema, generally by visits, within visit by forms (FIG. 2). Since a site may collect source data of the same kind across all visits on one or multiple pages of same type of form (for example, vitals for all visits are collected on one or multiple pages), we can use by form structure instead. In one embodiment, the operation module comprises study level process for adding sites, users and patients. When adding a new patient, the system will create eBinder folder structure automatically (FIG. 3).

The user roles and access control will be created according to Good Clinical Practice (GCP) defined in FDA guidance. The roles consist of (1) Principal Investigator (PI), (2) Clinical Research Coordinator (CRC), (3) Clinical Research Associate (CRA), and (4) data manager (DM). Only the PI, CRC and/or CRA if granted, have the right to access unmasked PII information (FIG. 1).

When patients visit study sites, the PI and/or CRC usually manually records the data on site-specific Data Collection Forms (sDCF) and keeps them in a patient binder (pBinder). Then, the CRC transcribes the data into corresponding Case Report Form (CRFs) in EDC, but often not immediately. This manual process at the site level may cause transcription errors and is extremely inefficient.

Figure 5:
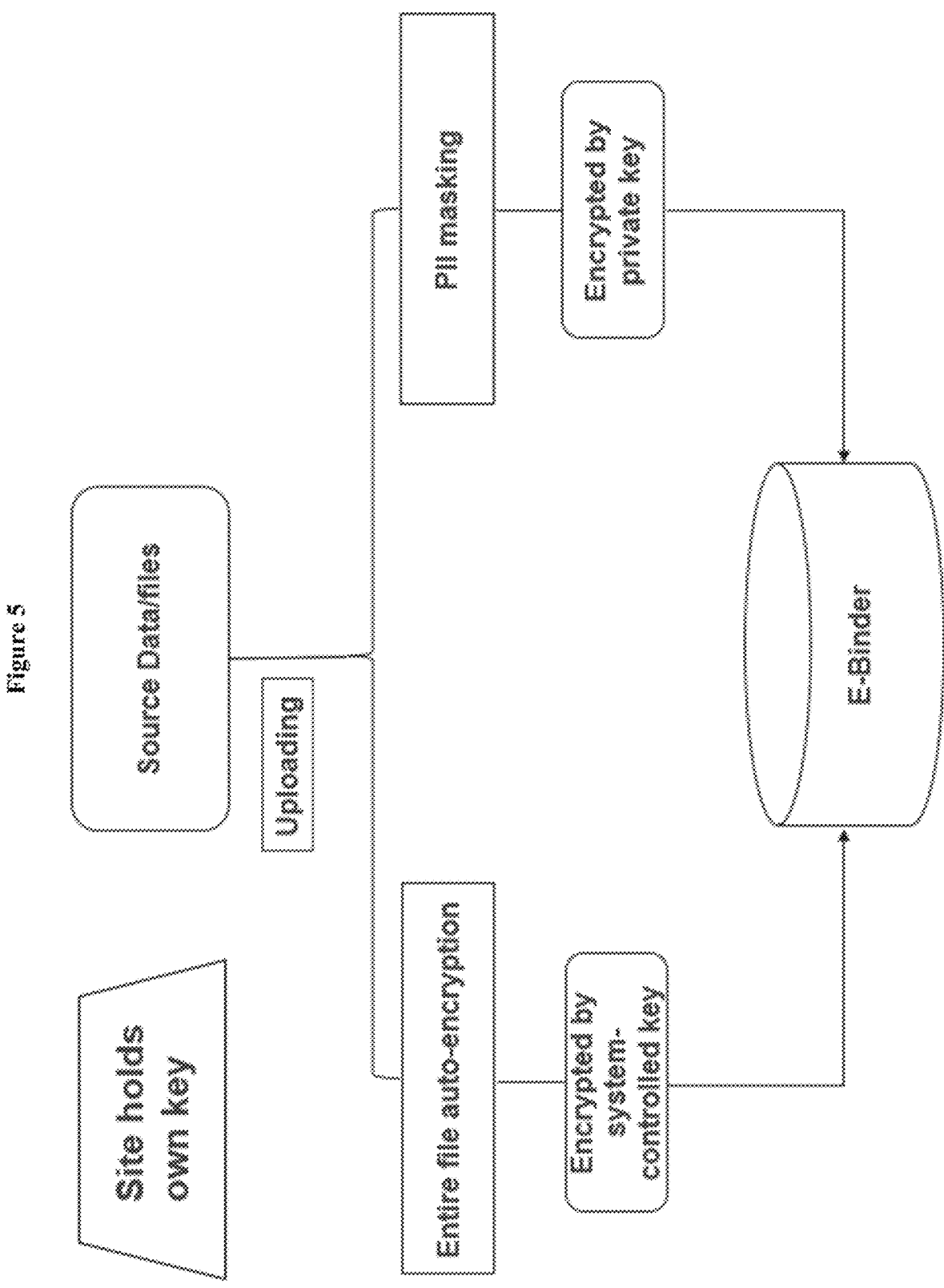
FIG. 5 illustrates encrypting and masking source data and files.
Figure 6:
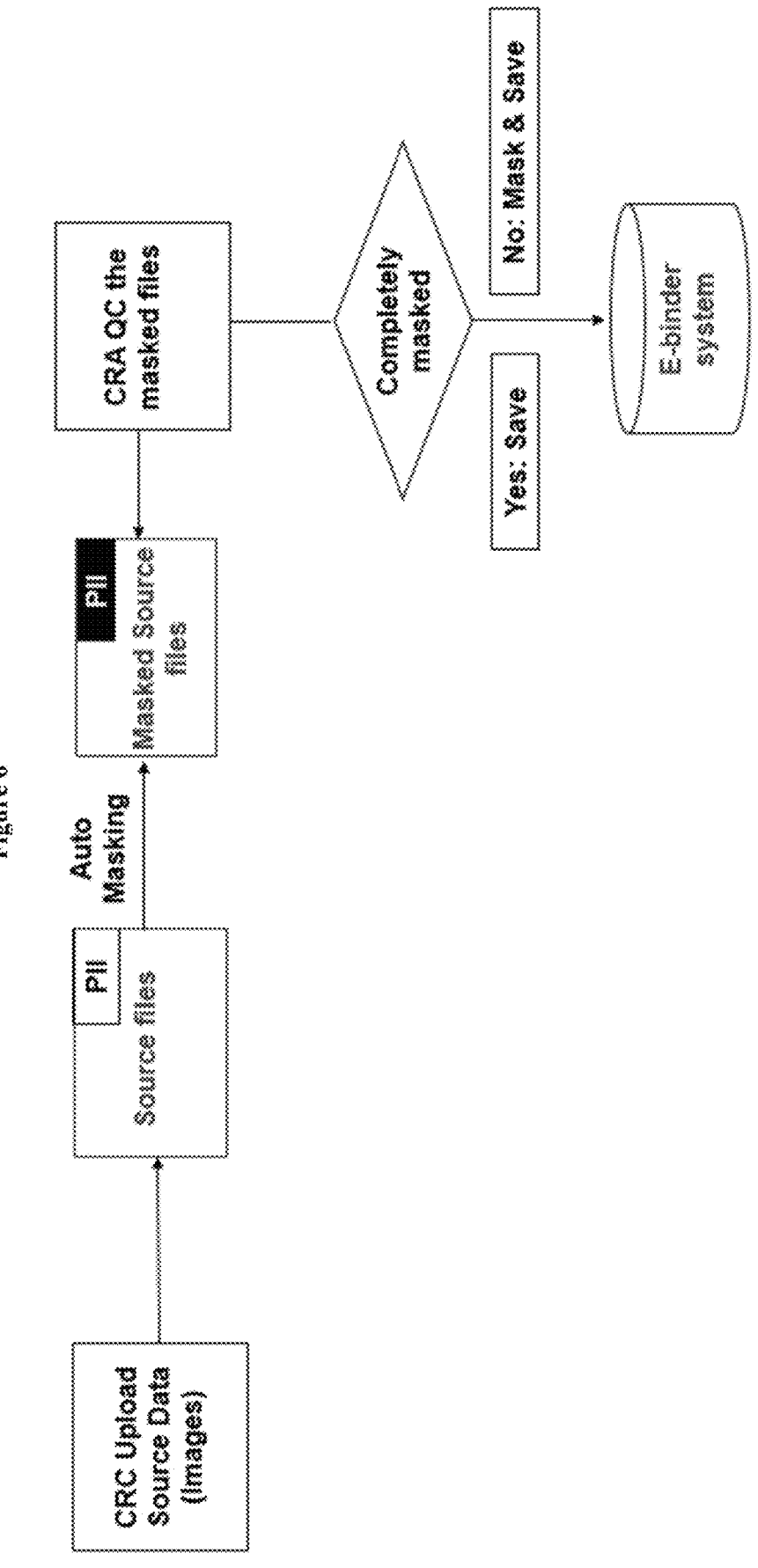
FIG. 6 illustrates source data uploading, PII Masking, and QC Process.

In one embodiment, CRC uploads the source data into the eBinder system. The system automatically masks PII information on the sources files prior to storage in eBinder database. In one embodiment, a private key for masking PII information will be held by the study site. A system-control key will be used for the non-PII portion of source files (FIG. 5). In one embodiment, the source files can only be reviewed by CRC and CRA. The uploaded source files may be distorted (rotated, shrunken or zoomed in) during scanning, CRA will login to the system to confirm the PII information is completely masked (FIG. 5).

Once CRA completes the quality control (QC) review and saves the source files, DM will be able to view the masked source files. In one embodiment (FIG. 7), the masked source files are automatically pushed to an OCR processor for converting the image files into machine readable plain text files in the JSON format.

In one embodiment (FIG. 8), machine readable plain text files in JSON format are automatically pushed to an HTML module for conversion into e-Source Form (eSF) format. This conversion not only makes it easier for the DM to compare the machine readable plaint text with its corresponding source file, but improves the efficiency of downstream processes. Compared with similar data in the JSON format, eSF machine readable plain text contains fewer redundant variables, making subsequent NLP/AI errors less likely, reducing the likelihood that the machine readable plaint text will exceed any NLP/AI input caps, and decreasing NLP/AI processor time.

In one embodiment (FIG. 13), the detailed process of the HTML module is illustrated.

In one embodiment (FIG. 9), the HTML format eSFs are automatically pushed to an NLP/AI module for conversion into machine understandable data tables and population into eCRF and EDC.

Figures 9, 10:
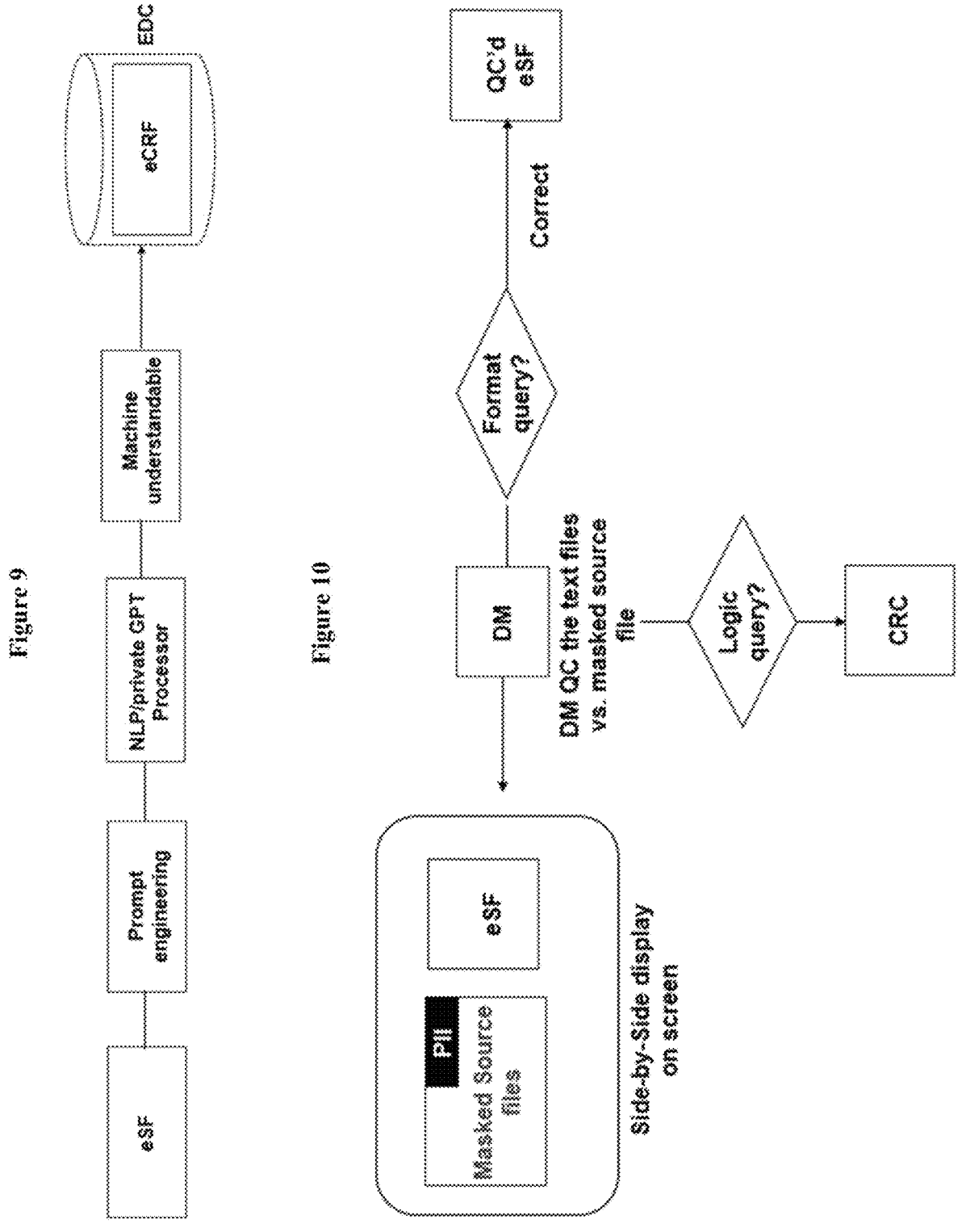
FIG. 9 illustrates NPL/GPT process for populating e-Source Form to eCRF.
FIG. 10 illustrates data manager (DM) QC e-Source Files.
Figure 12:
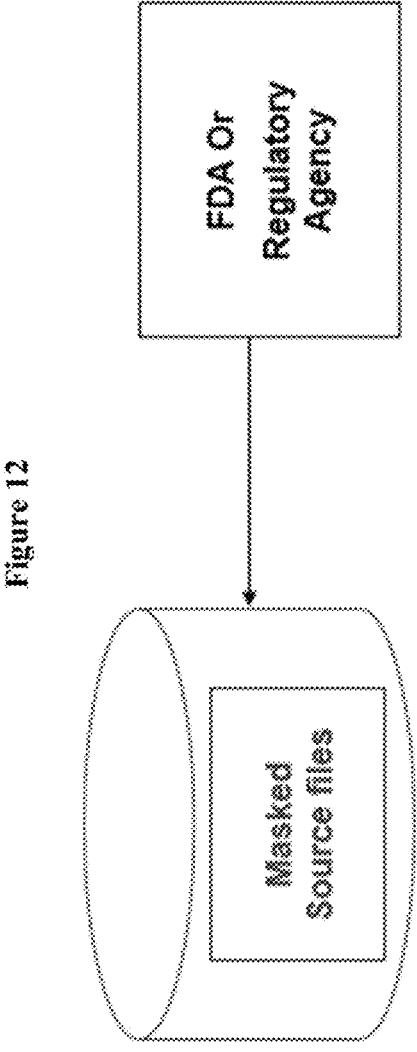
FIG. 12 illustrates FDA or Regulatory Agency accessing eBinder for Source Data Verification.

Once the original source file images are processed into EDC, system pre-built logic edit checks of data will be processed. If there are data queries, DM will perform data logic review as shown in one embodiment (FIG. 10).

Once DM completes data review and all queries are resolved, CRA can perform remote SDV as shown in one embodiment (FIG. 11).

In one embodiment, this invention provides a computerized system for automatically and seamlessly converting clinical trial source data into a plurality of key-value structured datasets and processing it into EDC datasets and eCRFs. The system comprises an eBinder system in electronic communication with a secure web application for receiving source data from clinical trial studies, an eBinder database for storing data, an encryption module for encrypting said source documents, a PII masking module for masking source data, an OCR module for converting source file images into machine readable plain text in the JSON format, an HTML module for converting said plain text in the JSON format into tabulated machine readable plain text in the HTML format, an NLP module for converting said machine readable plain text in the HTML format into machine understandable plain text, an AI module for populating source data into eCRFs, SDV module for displaying source data and associated converted data side-by-side for conducting remote SDV, and a viewing module for remotely accessing source data for regulatory review or auditing purposes.

In one embodiment, this invention provides a system for automatically and seamlessly converting clinical trial source data into a plurality of key-value structured datasets and processing it into EDC datasets and eCRFs. The system comprises a non-transitory computer readable storage media storing computer program instructions defined by the modules of the computerized system, a non-transitory computer readable storage media storing all data located on a secure, access restricted file server the modules comprising an encryption module for encrypting and decrypting data, and a web-based interface for displaying masked source data and the corresponding converted data side-by-side. Said modules comprise a masking module for automatically masking PII, an OCR module for converting source file images into machine readable plain text, a transposition module for converting said machine readable plain text into tabulated machine readable text, an NLP module for converting said tabulated machine readable plain text into machine understandable data, and a generator module for generating EDC datasets and eCRFs from said machine understandable data.

In one embodiment, the system's encryption module executes a dual-key encryption algorithm.

In one embodiment where the encryption module executes a dual-key encryption algorithm, one encryption key permits access to unmasked data and the other encryption key permits access to masked data.

In one embodiment, the machine readable plain text is in the JSON format.

In one embodiment, the tabulated machine readable plain text is in the HTML format.

In one embodiment, the NPL module utilizes a GPT.

In one embodiment, blockchain technologies are used to authenticate submission data and source files.

Throughout this application, various methods are implemented on non-transitory computer readable storage media.

Persons having ordinary skill in the art will understand that "non-transitory, computer readable storage media" may refer to one or more storage media capable of storing instructions for execution by a processor. For example, "non-transitory, computer readable storage media" comprises hard drives, solid state drives, random-access memory (RAM), and similar media.

Throughout this application, various publications are referenced by author and year. Full citations for the publications are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Many modifications and variations of the present invention are possible in light of the above teachings. It is, therefore, to be understood that within the scope of the appended claims, the invention can be practiced otherwise than as specifically described.

REFERENCES

[1] U.S. Food and Drug Administration. (2013, September). *Guidance for Industry: Electronic Source Data in Clinical Investigations*. Retrieved from https://www.fda.gov/media/85183/download

[2] Kellar, E., Bornstein, S., Caban, A., Crouthamel, M., Celingant, C., McIntire, P. A., . . . & Wilson, B. (2017). Optimizing the use of electronic data sources in clinical trials: the technology landscape. *Therapeutic Innovation & Regulatory Science,* 51, 551-567.

[3] Kellar, E., Bornstein, S. M., Caban, A., Célingant, C., Crouthamel, M., Johnson, C., . . . & Wilson, B. (2016). Optimizing the use of electronic data sources in clinical trials: the landscape, part 1. *Therapeutic Innovation & Regulatory Science,* 50(6), 682-696.

[4] TransCelerate Biopharma Inc. (2017). *Issues Related to Non-CRF Data Practices*. Retrieved from http://www.transceleratebiopharmainc.com/wp content/uploads/2018/01/eSource-Non-CRF-Data-Practices.pdf

What is claimed is:

1. A method for automatically and seamlessly converting clinical trial source data into key-value structured datasets and processing it into Electronic Data Capture datasets, wherein said clinical trial source data comprises site source file images, electronic medical records, and electronic patient-reported outcomes for use in conducting a clinical trial, the method comprising:
   a. defining a file structure for storing source data in an eBinder system;
   b. extracting source data from a plurality of sources;
   c. encrypting data using a dual-key encryption algorithm in which a private key held by a data owner for Patient Identifiable Information and shared-key for non-Patient Identifiable Information;
   d. masking of Patient Identifiable Information by a Clinical Research Coordinator and performing quality control of said masking by a Clinical Research Associate;
   e. converting masked source file images into machine readable plain text in the JavaScript Object Notation format using Optical Character Recognition technology;

f. transforming said JavaScript Object Notation format data into tabulated machine readable data in HyperText Markup Language format;
   g. using generative pretrained transformer technologies to correct format or spelling errors for transforming the machine-readable HyperText Markup Language data into machine understandable data;
   h. populating selected source data into correct data filed fields in Case Report Forms of Electronic Data Capture using generative pretrained transformer technology;
   i. displaying source files and converted data side-by-side for being able to conduct remote Source Data Verification; and
   j. providing a platform for verifying submission data against source files for regulatory review or auditing purposes.

2. A method for automatically and seamlessly converting clinical trial source data into key-value structured datasets and processing it into Electronic Data Capture datasets, wherein said clinical trial source data comprises site source file images, electronic medical records, and electronic patient-reported outcomes for use in conducting a clinical trial, the method comprising:
   a. defining a file structure for storing source data in an eBinder system;
   b. extracting source data from a plurality of sources;
   c. encrypting said source data using an encryption algorithm;
   d. masking Patient Identifiable Information;
   e. verifying the masking of said Patient Identifiable Information;
   f. converting said source file images into machine readable plain text using Optical Character Recognition technology;
   g. correcting any formatting or spelling errors in said machine readable plain text using a generative pretrained transformer;
   h. transforming said machine readable plain text into tabulated machine readable text using a generative pretrained transformer;
   i. converting said tabulated machine readable plain text into machine understandable plain text using a generative pretrained transformer,
   j. populating electronic Case Report Forms using said machine understandable plain text;
   k. displaying said populated electronic Case Report Forms and associated source data side-by-side; and
   l. verifying said electronic Case Report Forms against said associated source data.

3. The method of claim 2, wherein said encryption algorithm is a dual-key encryption algorithm.

4. The method of claim 3, wherein one encryption key permits access to unmasked data and the second encryption key permits access to masked data.

5. The method of claim 2, wherein said machine readable plain text is in the JavaScript Object Notation format.

6. A computerized system for automatically and seamlessly converting clinical trial source data into a plurality of key-value structured datasets and processing it into Electronic Data Capture datasets and electronic Case Report Forms, wherein said source data comprises site source file images, electronic medical records, and electronic patient-reported outcomes, all relating to the subjects of a clinical trial, the system comprising:
   a. a processor;

b. an eBinder system in electronic communication with a secure web application for receiving source data from clinical trial studies;

c. an eBinder database for storing data;

d. an encryption module for encrypting said source documents;

e. a Patient Identifiable Information masking module for masking source data;

f. an Optical Character Recognition module for converting source file images into machine readable plain text in the JavaScript Object Notation format;

g. a HyperText Markup Language module for converting said plain text in the JavaScript Object Notation format into tabulated machine readable plain text in the HyperText Markup Language format;

h. a generative pretrained transformer module for converting said machine readable plain text in the HyperText Markup Language format into machine understandable plain text;

i. a generative pretrained transformer module for populating source data into electronic Case Reporting Forms;

j. a Source Data Verification module for displaying source data and associated converted data side-by-side for conducting remote Source Data Verification; and k. a viewing module for remotely accessing source data for regulatory review or auditing purposes.

7. A computerized system for automatically and seamlessly converting clinical trial source data into a plurality of key-value structured datasets and processing it into Electronic Data Capture datasets and electronic Case Report Forms, wherein said source data comprises site source file images, electronic medical records, and electronic patient-reported outcomes, all relating to the subjects of a clinical trial, the system comprising:

a. a non-transitory computer readable storage media storing computer program instructions defined by the modules of the computerized system;

b. at least one computing unit coupled to the non-transitory computer readable storage media, the at least one computing unit configured to execute computer program instructions defined by the modules of the computerized system, the modules comprising:

i. an encryption module for encrypting and decrypting data;

ii. a masking module for automatically masking Patient Identifiable Information;

iii. an Optical Character Recognition module for converting source file images into machine readable plain text;

iv. a transposition module for converting said machine readable plain text into tabulated machine readable text;

v. a generative pretrained transformer module for converting said tabulated machine readable plain text into machine understandable data; and vi. a generator module for generating Electronic Data Capture datasets and electronic Case Report Forms from said machine understandable data;

c. a non-transitory computer readable storage media storing all data located on a secure, access restricted file server; and d. a web-based interface for displaying masked source data and the corresponding converted data side-by-side.

8. The system of claim 7, wherein said encryption module executes a dual-key encryption algorithm.

9. The system of claim 8, wherein one encryption key permits access to unmasked data and the other encryption key permits access to masked data.

10. The system of claim 7, wherein said machine readable plain text is in the JavaScript Object Notation format.

11. The method of claim 3, wherein said machine readable plain text is in the JavaScript Object Notation format.

12. The method of claim 4, wherein said machine readable plain text is in the JavaScript Object Notation format.

13. The system of claim 8, wherein said machine readable plain text is in the JavaScript Object Notation format.

14. The system of claim 9, wherein said machine readable plain text is in the JavaScript Object Notation format.

* * * * *